US006762311B2

(12) United States Patent
Rizkalla et al.

(10) Patent No.: US 6,762,311 B2
(45) Date of Patent: Jul. 13, 2004

(54) ETHYLENE OXIDE CATALYST

(75) Inventors: Nabil Rizkalla, Rivervale, NJ (US); Serguei Pak, Maywood, NJ (US); Andrew D. Schmitz, Rutherford, NJ (US)

(73) Assignee: Scientific Design Co., Ltd., Little Ferry, NJ (US)

( * ) Notice: Subject to any disclaimer, the term of this patent is extended or adjusted under 35 U.S.C. 154(b) by 0 days.

(21) Appl. No.: 10/056,710

(22) Filed: Nov. 13, 2001

(65) Prior Publication Data

US 2002/0107410 A1 Aug. 8, 2002

Related U.S. Application Data

(63) Continuation-in-part of application No. 09/562,320, filed on May 1, 2000, now abandoned.

(51) Int. Cl.⁷ ..................... C07D 301/10; B01J 27/02; B01J 27/06; B01J 23/48
(52) U.S. Cl. ..................... 549/534; 549/536; 502/216; 502/217; 502/218; 502/224; 502/344; 502/347
(58) Field of Search ................... 502/216, 217, 502/218, 224, 344, 347; 549/534, 536

(56) References Cited

U.S. PATENT DOCUMENTS

| | | | | |
|---|---|---|---|---|
| 4,829,044 A | * | 5/1989 | Boxhoorn et al. | 502/348 |
| 5,102,848 A | * | 4/1992 | Soo et al. | 502/218 |
| 5,145,824 A | * | 9/1992 | Buffum et al. | 502/216 |
| 5,854,167 A | * | 12/1998 | Rizkalla et al. | 502/216 |
| 5,905,053 A | * | 5/1999 | Rizkalla et al. | 502/216 |
| 5,958,824 A | * | 9/1999 | Rizkalla et al. | 502/216 |

* cited by examiner

*Primary Examiner*—Ngoc-Yen Nguyen
(74) *Attorney, Agent, or Firm*—William C. Long

(57) ABSTRACT

A silver catalyst for ethylene oxidation to ethylene oxide is provided containing a promoter combination consisting of critical amounts of an alkali metal component and a sulfur component, the catalyst being essentially free of rhenium and transition metal components; optionally the catalyst contains a fluorine component.

6 Claims, No Drawings

ETHYLENE OXIDE CATALYST

RELATED APPLICATIONS

This application is a continuation in part of Ser. No. 09/562,320 filed May 1, 2000 now abandoned.

BACKGROUND OF THE INVENTION

1. Field of the Invention

The present invention relates to a catalyst for the oxidation of ethylene to ethylene oxide consisting of a critical combination of silver, alkali metal such as cesium, and sulfur deposited on a support such as alpha alumina and to the production of ethylene oxide using the catalyst; a fluorine or chloride component optionally can be included. The catalyst is essentially free of rhenium or transition metal components.

2. Description of the Prior Art

Processes for the production of ethylene oxide involve the vapor phase oxidation of ethylene with molecular oxygen using a solid catalyst comprised of silver on a support such as alumina. There have been great efforts by many workers to improve the effectiveness and efficiency of the silver catalyst for producing ethylene oxide. U.S. Pat. No. 5,051,395 provides a comprehensive analysis of these efforts of prior workers.

Among the many prior teachings in this area is that of U.S. Pat. No. 4,007,135 (see also UK 1,491,447) which teaches variously silver catalysts for the production of ethylene and propylene oxides comprised of a promoting amount of copper, gold, magnesium, zinc, cadmium, mercury, strontium, calcium, niobium, tantalum, molybdenum, tungsten, chromium, vanadium, and/or preferably barium, in excess of any present in immobile form in the preformed support as impurities or cements (column 2, lines 1–15), silver catalysts for the production of propylene oxide comprising a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium, in excess of any present in immobile form in the preformed support as impurities or cements (column 2, lines 16–34), as well as silver catalysts for producing ethylene oxide or propylene oxide comprising (a) a promoting amount of sodium, cesium, rubidium, and/or potassium, and (b) magnesium, strontium, calcium and/or preferably barium in a promoting amount (column 3, lines 5–8).

U.S. Pat. No. 5,057,481, and related U.S. Pat. No. 4,908,343 are concerned with silver ethylene oxide catalysts comprised of cesium and an oxyanion of a group 3b to 7b element.

U.S. Pat. No. 3,888,889 describes catalysts suitable for the oxidation of propylene to propylene oxide comprised of elemental silver modified by a compound of an element from Group 5b and 6b. Although the use of supports is mentioned, there are no examples. The use of cesium is not mentioned.

European Publication 0 266 015 deals with supported silver catalysts promoted with rhenium and a long list of possible copromoters.

U.S. Pat. No. 5,102,848 deals with catalysts suitable for the production of ethylene oxide comprising a silver impregnated support also having thereon at least one cation promoter such as cesium, and a promoter comprising (i) sulfate anion, (ii) fluoride anion, and (iii) oxyanion of an element of Group 3b to 6b inclusive of the Periodic Table. Possibly for purposes of comparison since it is outside the scope of catalyst claimed, the patent shows at columns 21 and 22 a catalyst No. 6 comprised of Ag/Cs/S/F on a support, the Cs amount being 1096 ppm.

U.S. Pat. No. 5,486,628 describes a silver catalyst promoted with alkali metal, rhenium and a rare earth or lanthanide component.

U.S. Pat. No. 5,011,807 is concerned with an ethylene oxide catalyst comprised of silver, alkali metal, a transition metal, and sulfur on alumina support. Presented for comparative purposes are catalysts comprised of silver, alkali metal and sulfur on alumina support which provide results inferior to the transition metal containing catalysts.

In the context of the bewildering and vast number of references, many of them contradictory, applicant has discovered a novel and improved catalyst for the production of ethylene oxide.

BRIEF DESCRIPTION OF THE INVENTION

The present invention relates to an improved supported silver ethylene oxide catalyst containing a promoter combination consisting of a critical amount of both an alkali metal component, preferably cesium, together with a sulfur component, and to the catalyst preparation and use; the catalyst is essentially free of rhenium and transition metal components and optionally can contain a fluorine or chloride component.

DETAILED DESCRIPTION

Preferred catalysts prepared in accordance with this invention contain up to about 30% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–20% based on weight of total catalyst are preferred, while silver contents of 8–15% are especially preferred.

In addition to silver, the catalyst of the invention also contains a promoter combination consisting of critical amounts of alkali metal and sulfur. The critical amount of alkali metal promoter component is at least 1000 ppm expressed as alkali metal based on the catalyst weight; preferably the catalyst contains 1200–6000 ppm, alkali metal based on the catalyst weight. Preferably the alkali metal is cesium although lithium, sodium, potassium, rubidium and mixtures can also be used. Impregnation procedures such as are described in U.S. Pat. No. 3,962,136 are advantageously employed for addition of the cesium component to the catalyst.

Necessary also for practice of the invention is the provision of sulfur as a promoting catalyst component in a critical amount relative to the alkali metal. The sulfur component can be added to the catalyst support impregnating solution as sulfate, eg. cesium sulfate, ammonium sulfate, p-toluene sulfonic acid, and the like. U.S. Pat. No. 4,766,105 describes the use of sulfur promoting agents, for example at column 10, lines 53–60, and this disclosure is incorporated herein by reference. The amount of sulfur (expressed as the element) based on the weight of catalyst in accordance with the invention is critical and must be 40–150% of the equivalent amount necessary to form the alkali metal sulfate, eg. $Cs_2SO_4$, preferably 40–100% of this amount.

It has been found that the use of relatively high amounts of alkali metal, as above indicated, which normally would produce an inactive catalyst, when used in combination with the designated amounts of sulfur produces a catalyst having outstanding activity and selectivity.

The catalyst also optionally may contain a fluorine or chlorine promoter in amount expressed as the element of 10–300 ppm, preferably 30–100 ppm by weight based on the catalyst as an optional component. Ammonium fluoride or chloride, alkali metal fluoride or chloride, and the like can be used.

The catalysts are made with supports comprising alumina, silica, silica-alumina or combinations thereof. Preferred supports are those containing principally alpha-alumina, particularly those containing up to about 15 wt % silica.

Especially preferred supports have a porosity of about 0.1–1.0 cc/g and preferably about 0.2–0.7 cc/g. Preferred supports also have a relatively low surface area, i.e. about 0.2–2.0 $m^2/g$, preferably 0.4–1.6 $m^2/g$ and most preferably 0.5–1.3 $m^2/g$ as determined by the BET method. See J. Am. Chem. Soc. 60, 3098-16 (1938). Porosities are determined by the mercury porosimeter method; see Drake and Ritter, "Ind. Eng. Chem. anal. Ed.," 17, 787 (1945). Pore and pore diameter distributions are determined from the surface area and apparent porosity measurements.

For use in commercial ethylene oxide production applications, the supports are desirably formed into regularly shaped pellets, spheres, rings, etc. Desirably, the support particles may have "equivalent diameters" in the range from 3–10 mm and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

Preferably, the silver is added to the support by immersion of the support into a silver/amine impregnating solution or by the incipient wetness technique. The silver containing liquid penetrates by absorption, capillary action and/or vacuum into the pores of the support. A single impregnation or a series of impregnations, with or without intermediate drying, may be used, depending in part upon the concentration of the silver salt in the solution. To obtain catalyst having silver contents within the preferred range, suitable impregnating solutions will generally contain from 5–50 wt % silver, expressed as metal. The exact concentrations employed, of course, will depend upon, among other factors, the desired silver content, the nature of the support, the viscosity of the liquid, and solubility of the silver compound.

The impregnating solution, as already indicated, is characterized as a silver/amine solution, preferably such as is fully described in U.S. Pat. No. 3,702,259 the disclosure of which is incorporated herein by reference. The impregnation procedures described in U.S. Pat. No. 3,962,136 are advantageously employed for the cesium component.

Known prior procedures of predeposition, co-deposition and postdeposition of the various promoters can be employed.

After impregnation, any excess impregnating solution is separated and the support impregnated with silver and the promoter or promoters is calcined or activated. In the most preferred practice of the invention, calcination is carried out as described in commonly assigned U.S. Pat. No. 5,504,052 granted Apr. 2, 1996 and copending application Ser. No. 08/587,281 filed Jan. 16, 1996, the disclosures of which are incorporated herein by reference. The calcination is accomplished by heating the impregnated support, preferably at a gradual rate, to a temperature in the range 120–500° C. for a time sufficient to convert the contained silver to silver metal and to decompose the organic materials and remove the same as volatiles.

The impregnated support is maintained under an inert atmosphere while it is above 300° C. during the entire procedure. While not wishing to be bound by theory, it is believed that at temperatures of 300° C. and higher oxygen is absorbed in substantial quantities into the bulk of the silver where it has an adverse effect on the catalyst characteristics. Inert atmospheres as employed in the invention are those which are essentially free of oxygen.

An alternative method of calcination is to heat the catalyst in a stream of air at a temperature not exceeding 300° C., preferably not exceeding 280° C.

Catalysts prepared in accordance with the invention have improved performance, especially stability, for the production of ethylene oxide by the vapor phase oxidation of ethylene with molecular oxygen. These usually involve reaction temperatures of about 150° C. to 400° C., usually about 200° C. to 300° C., and reaction pressures in the range of from 0.5 to 35 bar. Reactant feed mixtures contain 0.5 to 30% ethylene and 3 to 15% oxygen, with the balance comprising comparatively inert materials including such substances as nitrogen, carbon dioxide, methane, ethane, argon and the like. Only a portion of the ethylene usually is reacted per pass over the catalyst and after separation of the desired ethylene oxide product and the removal of appropriate purge streams and carbon dioxide to prevent uncontrolled build up of inerts and/or by-products, unreacted materials are returned to the oxidation reactor.

A disadvantage of the prior art rhenium promoted catalysts has been the instability associated with such catalysts. In accordance with the present invention, the rhenium free catalysts have advantageously high selectivity and high stability.

The following examples illustrate the invention.

EXAMPLE 1

A silver solution was prepared using the following components

Parts are by Weight

Silver oxide—834 parts

Oxalic acid—442 parts

Deionized water—2808 parts

Ethylene Diamine—415 parts

Silver oxide was mixed with water, at room temperature, followed by the gradual addition of the oxalic acid. The mixture was stirred for 15 minutes and at that point the color of the black suspension of silver oxide had changed to the gray/brown color of silver oxalate. The mixture was filtered and the solids were washed with 3 liters of deionized water.

A container which contained the washed solids was placed in an ice bath and stirred while ethylene diamine and water (as a 72%/28% mixture) were added slowly in order to maintain the reaction temperature lower than 33° C. After the addition of all the ethylene diamine water mixture the solution was filtered at room temperature. The clear filtrate was utilized as a silver/amine stock solution for the catalyst preparation.

The support used for the examples was obtained from Norton Company and was made primarily of alpha-alumina in the form of 5/16 inch cylinders. The support had a surface area of 0.95 $m^2/g$, pore volume of 0.3 cc/g, and median pore diameter of 1.5 $\mu$.

For the examples, about 185 parts of the silver solution were mixed with varying amounts of:

1. CsOH solution, (8%Cs by weight in water),
2. ammonium fluoride, (3%F by weight in water)
3. ammonium hydrogen sulphate, (1%S by weight in water) the amounts of the promoter solutions being adjusted to give the promoter concentrations indicated in the tables.

The mixture of silver stock solution and promoter solutions was stirred to assure homogeneity, then added to 400 parts of the support. The wet catalyst was mixed for ten minutes and then calcined.

Calcination, the deposition of silver compound, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. It was increased, up to 400° C., as the catalyst passed through seven heating zones. After the heating zones the belt passed through a cooling zone that gradually cooled the catalyst to a temperature lower than 100° C. The total residence time in the furnace was 22 minutes. Atmosphere of the furnace was controlled through use of nitrogen flow in the different heating zones. In some instances, as indicated in the following table the calcination was carried out with air.

The catalysts were tested in a tube which was heated by a salt bath. A gas mixture containing 15% ethylene, 7% oxygen, and 78% inert, mainly nitrogen and carbon dioxide, was passed through the catalyst at 300 p.s.i.g., the temperature of the reaction was adjusted in order to obtain ethylene oxide productivity of 160 Kg per hour per m$^3$ of catalyst and this temperature is given in the Table.

The results of the catalyst tests are summarized in the following tables.

TABLE 1

| Example | Cs ppm | S ppm | S/2Cs Ratio | Temp °C. | Sel % | EO | Remarks |
|---|---|---|---|---|---|---|---|
| 1 (comparative) | 1050 | 0 | 0 | 258 | 77.3 | 1.5 | |
| 2 | 1050 | 85 | 0.672 | 235 | 84.5 | 1.56 | |

It has been discovered that when the concentration of S is 40–150% of the equivalent Cs level, the activity and selectivity of the catalyst are greatly enhanced. This benefit is especially evident when the concentration of S is 50–100% of the equivalent Cs level. The above two examples illustrate the effect of addition of S, wherein the reaction temperature dropped 23 degrees and the selectivity was higher by 7 points where S was added in the critical range as compared to a similar catalyst with no added S.

When the alkali metal component of the catalyst is added in high concentration the catalyst is virtually inactive. Addition of S, however, results in good performance as illustrated by the examples in the following Table:

TABLE 2

| Example | Cs ppm | S ppm | S/2Cs Ratio | Temp °C. | Sel % | Eo | Remarks |
|---|---|---|---|---|---|---|---|
| 3 (comparative) | 2450 | 0 | 0 | 260 | 30.0 | 0.03 | Catalyst is Inactive |
| 4 | 2551 | 307 | 1 | 243 | 85.0 | 1.5 | |
| 5 (comparative) | 1166 | 0 | 0 | 260 | 65.2 | 0.25 | Catalyst is Inactive |
| 6 | 1092 | 76 | 0.58 | 253 | 83.3 | 1.5 | |
| 7 (comparative) | 4007 | 0 | 0 | 260 | 25 | .001 | Catalyst is Inactive |
| 8 | 3953 | 408 | 0.86 | 254 | 83.6 | 1.5 | |
| 9 | 5418 | 565 | 0.87 | 243 | 83.8 | 1.37 | |

In this group of examples, it can be seen that the addition of S gave a sharp increase in the catalyst's selectivity and activity; compare examples 3 and 4, also 5 and 6 as well as examples 7 and 8.

TABLE 3

| Example # | Cs ppm | S ppm | S/2Cs Ratio | % Ag | Promoters | Temp °C. | Sel % | EO |
|---|---|---|---|---|---|---|---|---|
| 10 | 1459 | 180 | 1.0 | 12.27 | Cs$_2$SO$_4$/NH$_4$Cl | 234 | 85.9 | 1.5 |
| 11 | 2282 | 274 | 1.0 | 11.09 | Cs$_2$SO$_4$ | 242 | 85.9 | 1.5 |
| 12 | 1566 | 98 | 0.52 | 11.96 | Cs$_2$SO$_4$/CsOH/NH$_4$Cl | 239 | 86.6 | 1.5 |
| 13 | 1480 | 98 | 0.55 | 11.98 | Cs$_2$SO$_4$/CsOH/NH$_4$Cl | 245 | 86.7 | 1.5 |
| 14 | 1460 | 98 | 0.56 | 11.93 | Cs$_2$SO$_4$/CsOH/NH$_4$Cl | 243 | 86.8 | 1.5 |
| 15 | 1580 | 115 | 0.6 | 11.68 | Cs$_2$SO$_4$/CsOH/NH$_4$Cl | 243 | 87.0 | 1.5 |

In the above tables, a S/2Cs ratio of 1 represents 100% of the equivalent amount of sulfur to form cesium sulfate. A S/2Cs of 0.86 represents 86% of the equivalent amount of sulfur to form cesium sulfate, for example.

We claim:

1. A rhenium and transition metal free catalyst for the oxidation of ethylene to ethylene oxide comprised of silver on a solid support and containing a promoter combination consisting essentially of (1) an alkali metal component in amount of 1200 to 3000 ppm, based on the weight of the catalyst; and (2) a sulfur component in amount of 40–150% of the equivalent weight necessary to form the alkali metal sulfate.

2. The catalyst of claim 1 wherein the alkali metal component is cesium.

3. The catalyst of claim 1 wherein the support is alpha alumina.

4. The catalyst of claim 1 comprised by weight of 5–20% silver.

5. The method for producing ethylene oxide which comprises reacting ethylene and molecular oxygen in the presence of the catalyst of claim 1.

6. A rhenium and transition metal free catalyst for the oxidation of ethylene to ethylene oxide comprised of silver on a solid support and containing a promoter combination consisting essentially of (1) an alkali metal component in amount of 1200 to 3000 ppm, based on the weight of the catalyst; (2) a sulfur component in amount of 40–150% of the equivalent weight necessary to form the alkali metal sulfate; and (3) a fluorine component in amount of 10–300 ppm.

* * * * *